(12) United States Patent
Ollmar et al.

(10) Patent No.: US 9,017,258 B2
(45) Date of Patent: Apr. 28, 2015

(54) DETERMINATION OF BIOLOGICAL CONDITIONS USING IMPEDANCE MEASUREMENTS

(75) Inventors: Stig Ollmar, Huddinge (SE); Peter Aberg, Lidkoping (SE); Ingrid Nicander, Stockholm (SE)

(73) Assignee: Scibase AB, Stockholm (SE)

( * ) Notice: Subject to any disclaimer, the term of this patent is extended or adjusted under 35 U.S.C. 154(b) by 2232 days.

(21) Appl. No.: 10/682,372

(22) Filed: Oct. 10, 2003

(65) Prior Publication Data

US 2004/0127780 A1 Jul. 1, 2004

Related U.S. Application Data

(60) Provisional application No. 60/417,561, filed on Oct. 11, 2002.

(51) Int. Cl.
| | |
|---|---|
| A61B 5/00 | (2006.01) |
| A61B 5/04 | (2006.01) |
| A61B 5/05 | (2006.01) |
| A61B 5/053 | (2006.01) |
| A61B 5/06 | (2006.01) |
| A61B 5/145 | (2006.01) |

(52) U.S. Cl.
CPC .............. *A61B 5/0531* (2013.01); *A61B 5/061* (2013.01); *A61B 5/14532* (2013.01); *A61B 5/411* (2013.01); *A61B 5/444* (2013.01); *A61B 5/6839* (2013.01)

(58) Field of Classification Search
CPC .................................................... A61B 5/0531
USPC ............... 600/300, 301, 306, 309, 345–366, 600/372–397, 547, 546, 481, 557; 607/149
See application file for complete search history.

(56) References Cited

U.S. PATENT DOCUMENTS

| | | | |
|---|---|---|---|
| 5,036,861 A | 8/1991 | Sembrowich et al. | |
| 5,115,133 A | 5/1992 | Knudson | |
| 5,146,091 A | 9/1992 | Knudson | |
| 5,179,951 A | 1/1993 | Knudson | |
| 5,222,496 A | 6/1993 | Clarke et al. | |
| 5,353,802 A | 10/1994 | Ollmar | |
| 5,433,197 A | 7/1995 | Stark | |
| 5,508,203 A | 4/1996 | Fuller et al. | |
| 6,334,856 B1 | 1/2002 | Allen et al. | |
| 6,379,324 B1* | 4/2002 | Gartstein et al. | 604/22 |
| 6,451,240 B1* | 9/2002 | Sherman et al. | 264/504 |

(Continued)

FOREIGN PATENT DOCUMENTS

| | | |
|---|---|---|
| CA | 2 318 735 A1 | 7/2000 |
| WO | WO 92/06634 | 4/1992 |

(Continued)

OTHER PUBLICATIONS

Griss et al. "Micromachined electrodes for biopotential measurements." Journal of Microelectromechanical Systems, vol. 10, issue 1, Mar. 2001, pp. 10 to 16.

Emtestam, I. et al. "Electrical impedance of nodular basal cell carcinoma: a pilot study." Dermatology, vol. 197, 1998, pp. 313 to 316.

Kapoor, S. "Bioelectric impedance techniques for clinical detection of skin cancer." Thesis, University of Missouri-Rolla, 2001.

(Continued)

*Primary Examiner* — Navin Natnithithadha
(74) *Attorney, Agent, or Firm* — Birch, Stewart, Kolasch & Birch, LLP

(57) ABSTRACT

Apparatus and methods for the diagnostics of biological conditions using impedance measurements.

30 Claims, 13 Drawing Sheets

(56) References Cited

U.S. PATENT DOCUMENTS

| | | | |
|---|---|---|---|
| 6,471,903 B2* | 10/2002 | Sherman et al. | 264/328.1 |
| 6,501,976 B1* | 12/2002 | Sohrab | 600/347 |
| 6,565,532 B1* | 5/2003 | Yuzhakov et al. | 604/142 |
| 6,622,035 B1* | 9/2003 | Merilainen et al. | 600/391 |
| 6,788,966 B2* | 9/2004 | Kenan et al. | 600/372 |
| 6,922,586 B2* | 7/2005 | Davies | 600/547 |
| 7,103,398 B2* | 9/2006 | Sieburg | 600/393 |
| 2003/0216661 A1* | 11/2003 | Davies | 600/547 |
| 2004/0054393 A1* | 3/2004 | Stemme et al. | 607/149 |
| 2004/0152997 A1* | 8/2004 | Davies | 600/547 |
| 2005/0203436 A1* | 9/2005 | Davies | 600/547 |
| 2006/0100488 A1* | 5/2006 | Davies | 600/306 |

FOREIGN PATENT DOCUMENTS

| | | |
|---|---|---|
| WO | WO 95/04496 | 2/1995 |
| WO | WO 98/04190 | 2/1998 |
| WO | WO 99/39627 | 8/1999 |
| WO | WO 01/26538 | 4/2001 |
| WO | WO 01/52731 | 7/2001 |

OTHER PUBLICATIONS

Aberg, P et al. "Assessment of skin lesions and skin cancer using simple electrical impedance indices." Skin Research Technology, vol. 9, 2003, pp. 257-261.

Beetner, D.G. et al. "Differentiation among basal cell carcinoma, benign lesions, and normal skin using electric impedance." IEEE Trans. Biomed. Eng., vol. 50, 2003, pp. 1020-1025.

Dua, R. et al. "Detectionof basal cell carcinoma using electrical impedance and neural networks." IEEE Trans. Biomed. Eng., received for publication Dec. 20, 2002; accepted for publication 2003; in press 2004.

Ollmar et al., "Electrical impedence for estimation of irritation in oral mucosa and skin", Medical Progress through Technology, vol. 21, No. 1, Feb. 1, 1995, pp. 29-37.

Aberg et al., "Assessment of skin lesions and skin cancer using simple electrical impedance indices", Skin Research and Technology, vol. 9, 2003, pp. 257-261.

\* cited by examiner

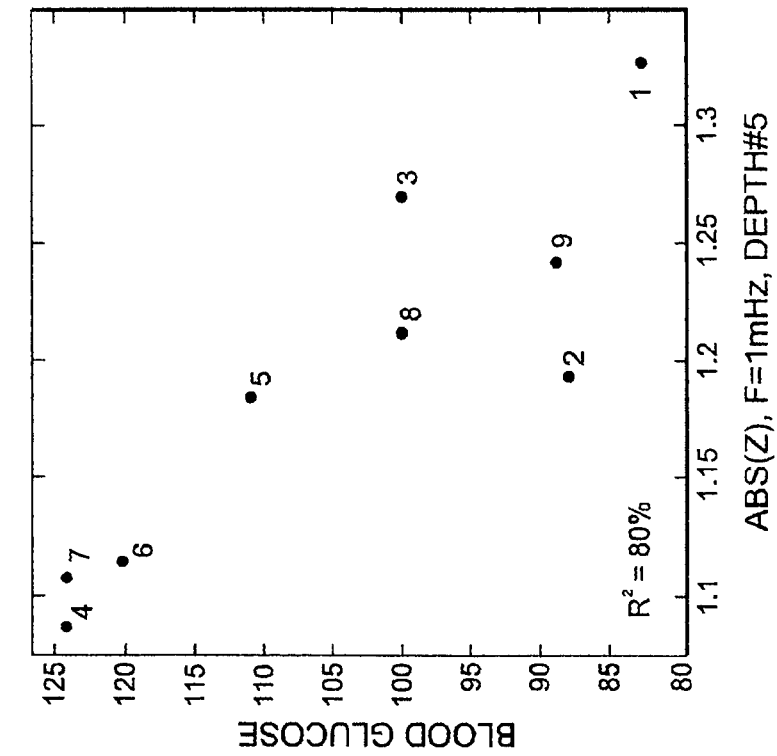
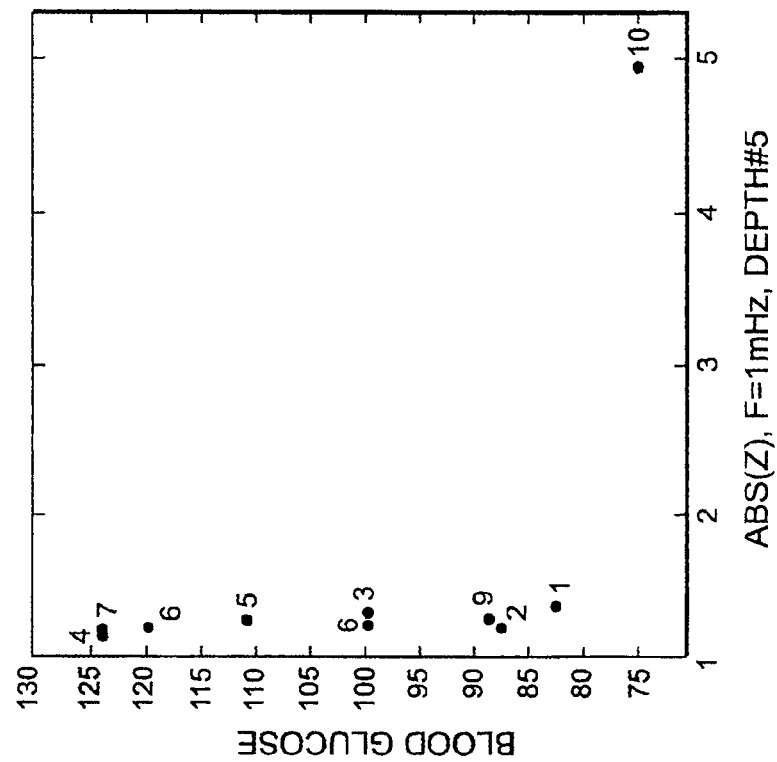
Figure 6(b)
Figure 6(a)

DETERMINATION OF BIOLOGICAL CONDITIONS USING IMPEDANCE MEASUREMENTS

This application claims priority from U.S. patent application Ser. No. 60/417,561, filed on Oct. 11, 2002, the contents of which are incorporated herein by reference.

FIELD OF THE INVENTION

This invention is in the field of diagnostics of biological conditions. In one aspect, the invention involves in vivo evaluation of the level of a substance in the blood of a subject, particularly blood glucose levels. In another aspect, the invention involves diagnosing a diseased condition of the skin of a subject, particularly the presence of a skin cancer, e.g. basal cell carcinoma or malignant melanoma, a squamous cell carcinoma or precursors thereof. In both instances, the determination is based on skin impedance measurements.

BACKGROUND OF THE INVENTION

Non-invasive methods of making biological determinations are generally desirable over invasive techniques that involve the taking of samples. Non-invasive techniques can be more convenient, e.g., less painful, involve less risk of infection, etc. Non-invasive techniques for evaluating blood glucose levels have been described in the patent literature:

| Application No. | Publication No. | Publication Date | Name |
|---|---|---|---|
|  | U.S. Pat. No. 5,036,861 | Aug. 6, 1991 | Sembrowich et al. |
|  | U.S. Pat. No. 5,115,133 | May 19, 1992 | Knudson |
|  | U.S. Pat. No. 5,146,091 | Sep. 8, 1992 | Knudson |
|  | U.S. Pat. No. 5,197,951 | Jan. 19, 1993 | Knudson |
|  | U.S. Pat. No. 5,222,496 | Jun. 29, 1993 | Clarke et al. |
| PCT/US 94/08816 | WO 95/04496 | Feb. 16, 1995 | Solid State Farms, Inc. |
|  | U.S. Pat. No. 5,433,197 | Jul. 18, 1995 | Stark |
| PCT/US 97/13267 | WO 98/04190 | Feb. 5, 1998 | Dermal Therapy (Barbados) Inc. |
| PCT/US 98/02037 | WO 99/39627 | Aug. 12, 1999 | Dermal Therapy (Barbados) Inc. |
| PCT/IB 00/01464 | WO 01/26538 | Oct. 13, 2000 | Psstrunk, et al. |

SUMMARY OF THE INVENTION

A summary of the invention in its various aspects is provided in the attached claims, bearing in mind that those skilled in the art will understand that a variety of possible combinations and subcombinations of the various elements described in the claims and throughout this specification exist, and all of these combinations and subcombinations should be considered to be within the inventors' contemplation though not explicitly enumerated here. This is also true of the variety of aspects of the processes and the combinations and subcombinations of elements thereof.

DESCRIPTION OF DRAWINGS

The invention is described in greater detail below, with reference to the attached figures, in which:

FIG. 2 shows representative Bode plots of impedance (left hand axis, kOhms) and phase (right hand axis; degrees) as a function of frequency number (31 logarithmically distributed frequencies from 1 kHz to 1 MHz) for subject B. The results shown in FIG. 2(a) were obtained using a conventional probe and those shown in FIG. 2(b) were obtained using a spiked electrode.

FIG. 6(a) shows a scatter plot of subject B's blood glucose vs. magnitude of impedance at 1 MHz and depth setting number 5 measured with the spiked electrode with (left) outlier reading number 10. FIG. 6(b) is the same plot without the outlier;

FIG. 8 shows representative Bode plots of impedance (left hand axis; kOhm) and phase angle (right hand axis; degrees) as a function of frequency (kHz), plotted logarithmically, obtained at five depth settings using a spiked electrode.

DESCRIPTION OF PREFERRED EMBODIMENTS

Figure 1A:
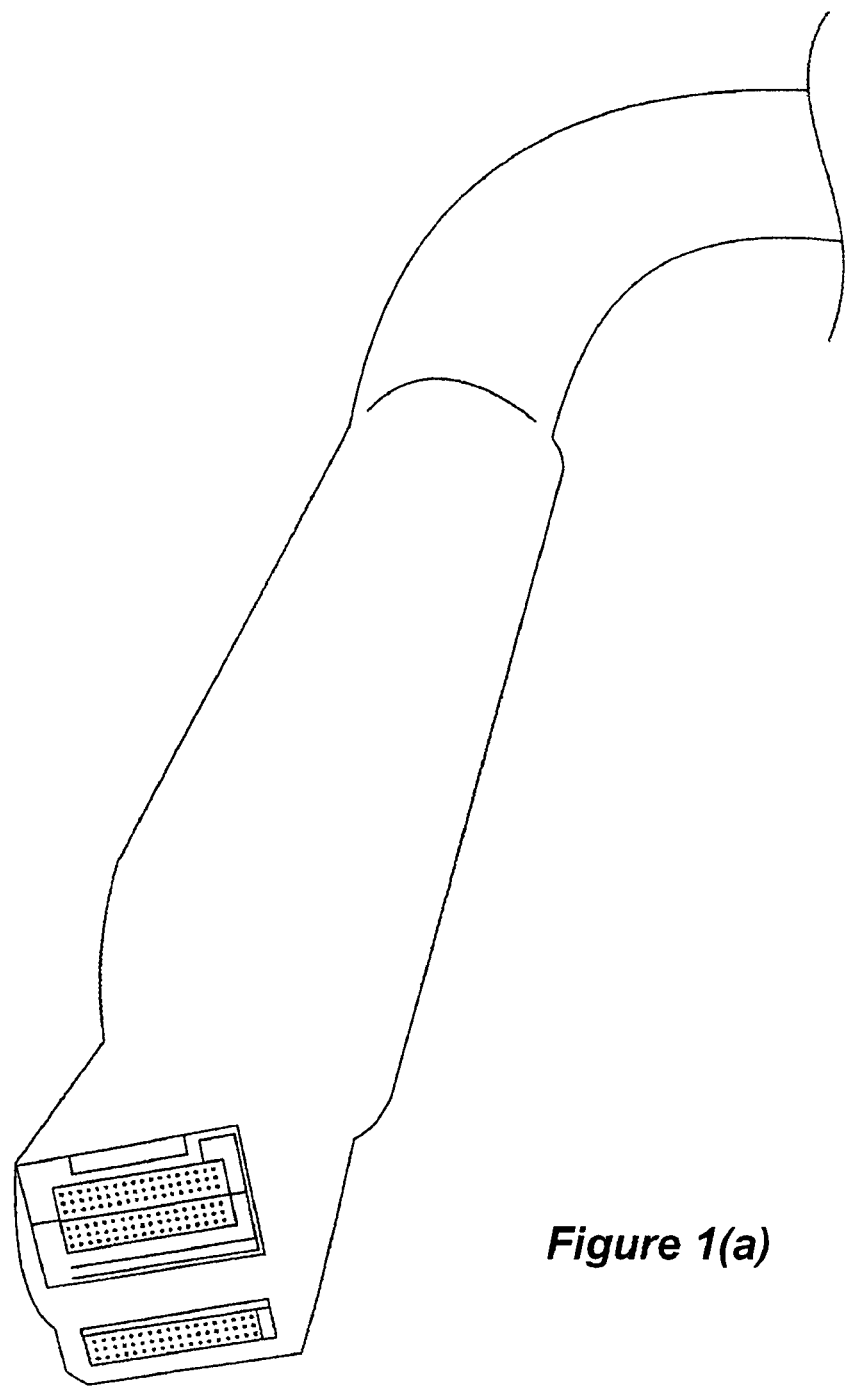
FIG. 1(a) shows a spiked electrode of the present invention.
Figure 1B:
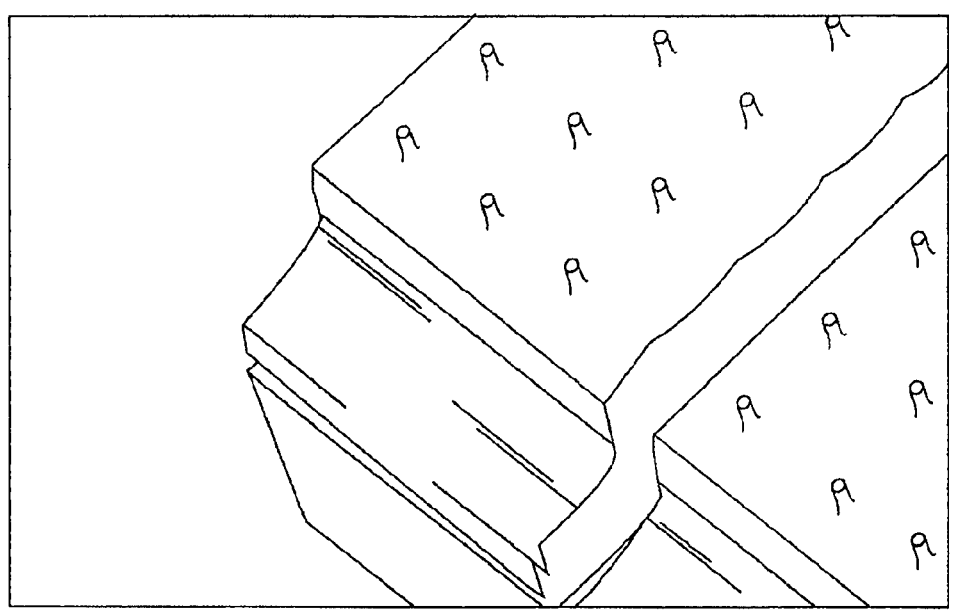
FIG. 1(b) shows details of the spiked array given as electron micrograph.

An apparatus for use according to the present invention can generally be regarded as a combination of the device described in international patent application No. PCT/SE 91/00703, published under WO 92/06634 on Apr. 30, 1992 and the "spiked" electrode described in international patent application No. PCT/IB 01/00059, published under WO 01/52731 on Jul. 26, 2001 or in an article entitled "Micromachined Electrodes for Biopotential Measurements" published in the Journal of Microelectromechanical Systems 10(1), pp 10-16, on March 2001 by Griss et al. In particular, PCT-SE 91/0073 in the Abstract discloses "device for depth-selective, non-invasive, local measurement of electrical impedance of organic and biological material such as tissues from vegetable or animal origin comprising a probe . . . with a number of electrodes . . . driven from an electronic control unit . . . ,in such a way that the electric current path defining the actual tissue under test is dependent upon a control signal . . . "The electrode used in the tests described below, however, is a variation of that described by Griss et al., and is shown if FIGS. 1(a) and 1(b). The probe includes of a number of electrodes, at least three according to No. PCT/SE 91/00703, and in the present invention each electrode of the probe has a spiked surface, which permits measurements to be made at a variety of skin depths. The probe is illustrated in FIG. 1(b), the probe being viewed looking down onto its spikes (a bottom plan view). The probe includes three rectangular areas or bars each bar containing an array of 35 (7×5) spikes. Each bar is 1 mm wide and 5 mm long. The distance between the closest bars is 0.2 mm, and the wider between the second and third bars is 1.8 mm. The active part of the probe is thus about 5×5 mm. Each spike has a length of approximately 150 micrometer, as measured from its base, and a thickness of approximately 25 micrometer. The spikes are sharpened cylinders, i.e. are needle-like, and spaced approximately 200 micrometers from each other, center to center. The spikes were of silicon and covered with gold approximately 2 micrometer thick. Any material comprising a conductive surface with similar dimensions would work, but should be selected to be biocompatible.

The apparatus, without the spiked probe known as the SciBase II depth selective spectrometer, may be obtained from SciBase AB of Huddinge, Sweden. The pin assignment for the probe connector was as follows:
1. <START> button
2. sense (first electrode illustrated FIG. 1(b); use coaxial (conventional probe) screen 3.
3. gnd (for sense)
4. near exciter (second (middle) electrode illustrated in FIG. 1(b); use coaxial (conventional probe) screen 5.
5. gnd (for near injection).
6. gnd.
7. far exciter (third (right-most) electrode illustrated in FIG. 1(b); use coaxial (conventional probe) screen 8.
8. gnd (for far injection).
9. chassis.
10. reserved.
11. reserved.
12. gnd.
13. gnd.
14.
15. charger.

Blood Glucose Levels

Tests were conducted using the foregoing apparatus to determine the feasibility of using such apparatus in determining blood glucose levels of human beings. Trials were conducted on two individuals, subjects A and B. Subject A suffers from atopic dermatitis, making the subject a relatively poor candidate for a non-invasive determination involving a skin measurement.

Tests were thus carried out (i) to assess the correlation between skin impedance measured using the spiked electrodes and the blood glucose, and (ii) to compare the glucose correlation of impedance measured with a conventional probe and the spiked electrodes.

Two sites, one on each arm, were marked. One site was used for the spiked probe and the other for the conventional probe. Blood glucose levels were measured directly using the Glucometer Elite (available from Elite Glucometer, Miles Canada, Diagnostics Division, Division of Bayer). The sites were soaked for 60 seconds prior to each impedance measurement using 0.9% saline solution and stopwatch. Impedance was measured using the SciBase II depth selective spectrometer at 31 logarithmically distributed frequencies from 1 kHz to 1 MHz at five depth settings, as described in PCT/SE/00703.

The correlation between impedance and blood glucose was evaluated in three steps with increasing complexity of the regression models. The first step is linear regression between raw impedance and blood glucose for each frequency, depth setting and impedance presentation (magnitude, phase, real part, and imaginary part). The second step is linear regression between indices and blood glucose. The indices are described in detail below. The last step is partial least squares regression (PLS) models of full impedance spectra and glucose levels.

Figure 2B:
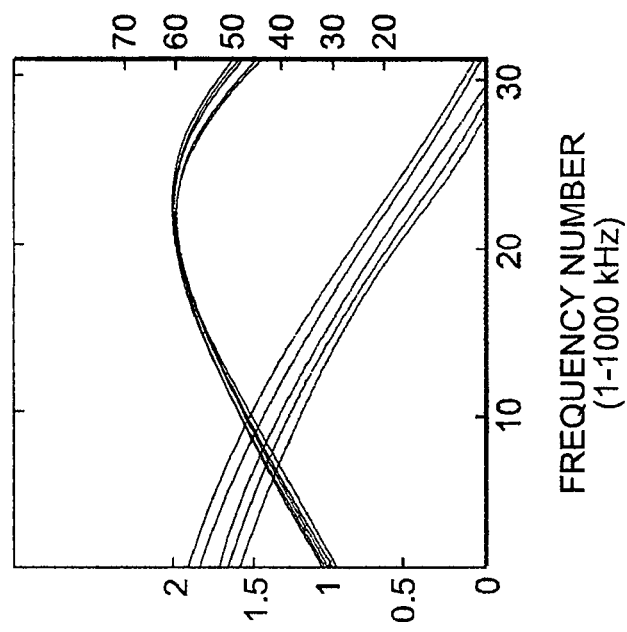
In FIG. 2(b), the phase plots display a local maximum around frequency number 21.
Figure 2A:
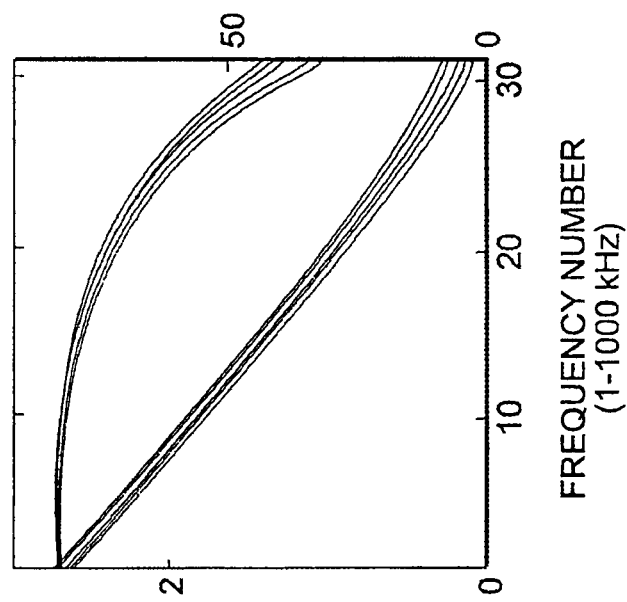
In FIG. 2(a), the lower set of curves shows the magnitude of the impedance (at various depths) and the corresponding phase is shown by the upper set of curves.

As indicated in FIG. 2, the magnitude of the impedance measured with the regular probe (FIG. 2(a)) was found to be much higher along with the phase, and the characteristic frequency was lower. Hence, impedance measured with the conventional probe was significantly different from the spiked electrodes.

Figure 3:
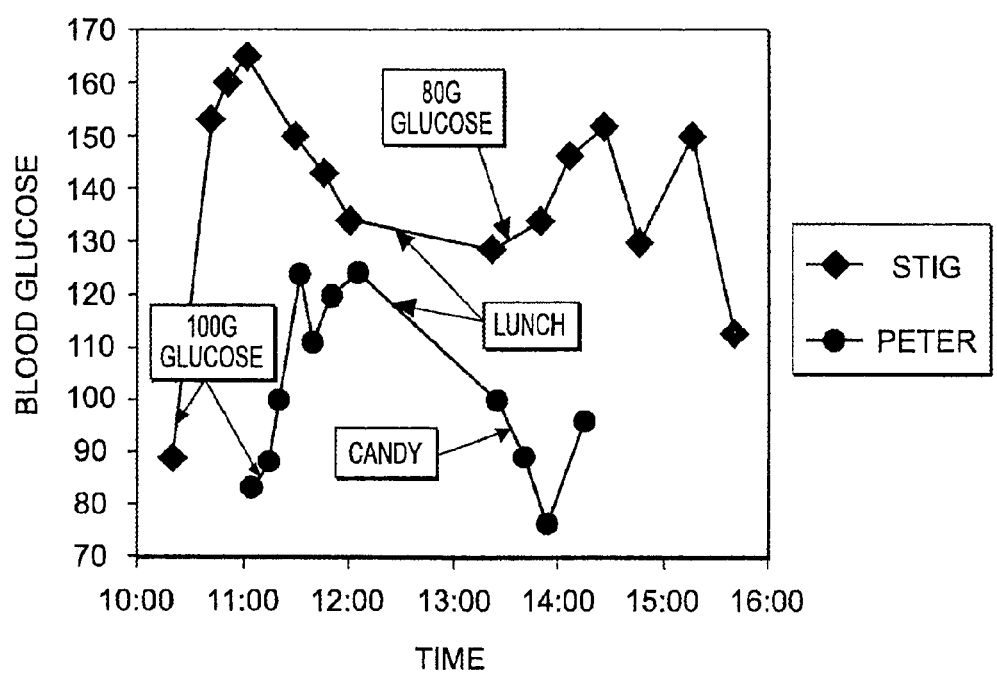
FIG. 3 shows the blood glucose level as determined directly over the course of the tests for each subject. Subject A (◆), subject B (●)
Figure 4B:
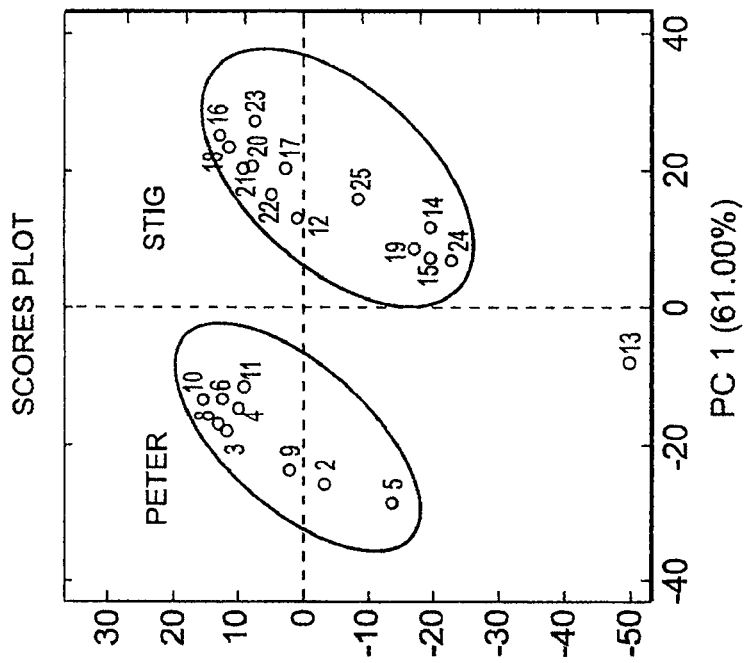
FIG. 4(b) is a corresponding plot for each subject obtained with the conventional probe. In both plots, subject A is to the right and subject B is to the left of the figure.
Figure 4A:
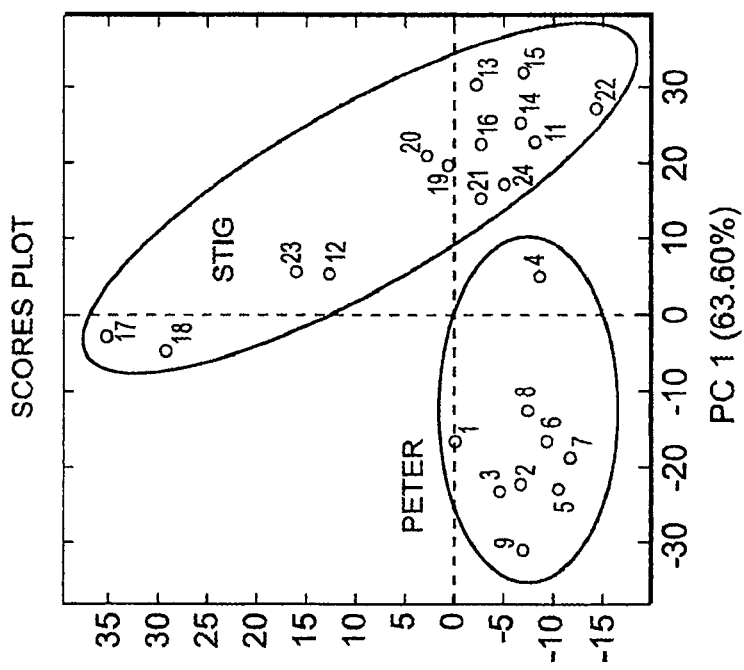
FIG. 4(a) shows a scatter plot of PCA (principle component analysis) for each subject (t1 vs. t2) obtained with the spiked electrode.

The tests were carried out over about 5 hours. The electrodes with spikes used to measure impedance of subject B broke down after approximately 10-11 readings. The glucose levels for subject A and B, as measured directly, are shown in FIG. 3. The glucose levels of subject A were generally higher than for subject B, and the impedance of the two volunteers was also found to be different, as indicated in FIG. 4. This indicates that it might not be possible to use one calibration model for these subjects.

The four indices (MIX, PIX, RIX, and IMIX) were originally made to normalise impedance spectra of the spectrometer. It was found that the four indices described a substantial part of the variations in the impedance spectra and were useful in skin irritation assessments, but not necessarily in glucose quantifications. Therefore, new indices, ix, were made using the frequencies, f, depth settings, d, for all impedance presentations, X, according to (1).

$$ix(i, j, k, l, m, n) = \frac{X_i(f_j, d_k)}{X_l(f_m, d_n)} \quad (1)$$

Figure 5B:
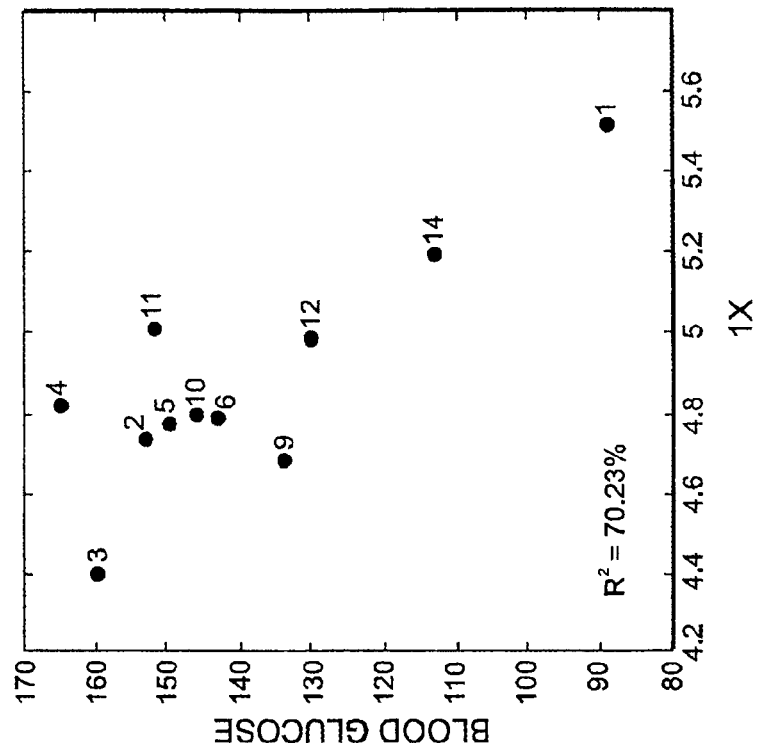
FIG. 5(b) shows the same plot without outliers, readings number 7, 8, and 13.
Figure 5A:
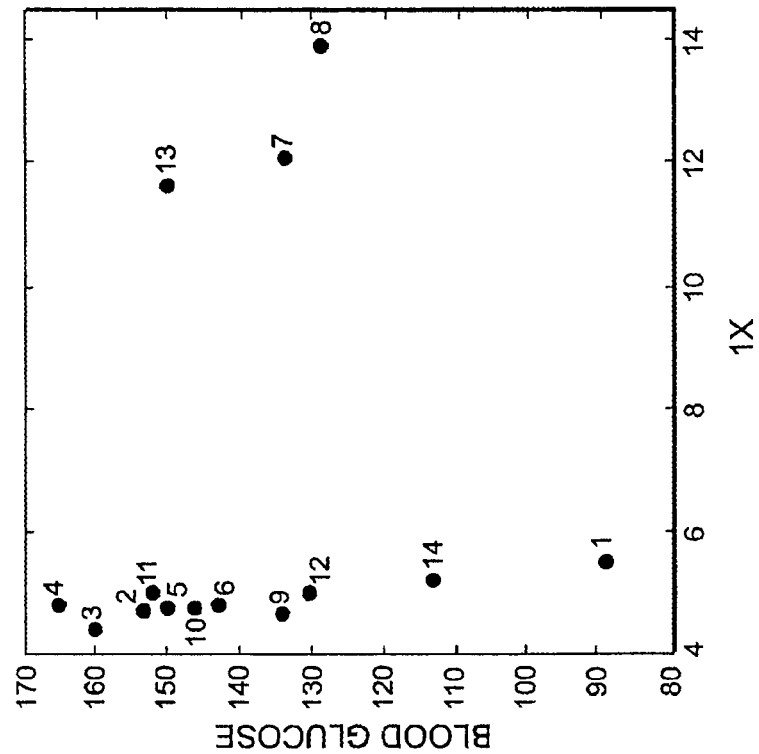
FIG. 5(a) shows a scatter plot of measured blood glucose and index with outliers of subject A obtained with the spiked electrode.

$i, k \in 1 \ldots 4$
$X_1=|Z|, X_2=\theta, X_3=\text{Re}(Z), X_4=\text{Im}(Z)$
$f_j, f_m \in 1 \text{ kHz} \ldots 1 \text{ Mhz}$
$d_k, d_n \in 1 \ldots 5$ Three impedance readings were abnormal and excluded from the data analysis. Correlation coefficient (R2) of linear regression between an impedance index of the results obtained with the spiked electrode and subject A's blood glucose was 70% (n=11). This is shown in FIG. 5. The new index used in this analysis is based on only two frequencies, each frequency measured at different depth settings, and is defined as:

$$ix = \frac{\text{Re}(Z_{20\,kHz, depth\,\#5})}{|Z_{500\,kHz, depth\,\#3}|}$$

In the case of the conventional probe, no significant correlation was found between impedance measured and blood glucose for subject A.

In the case of subject B and the results obtained with the spiked electrode, there was one reading with abnormal impedance. The measurement was made just before the spiked probe broke down and it is believed that the impedance of the actual reading was abnormal because the spiked probe was beginning to malfunction when the last measurement was made. Linear regression between the magnitude of the raw impedance at high frequencies and deep depths and blood glucose showed good correlation, $R^2=80\%$ (n=9). See FIG. 6.

Figure 7:
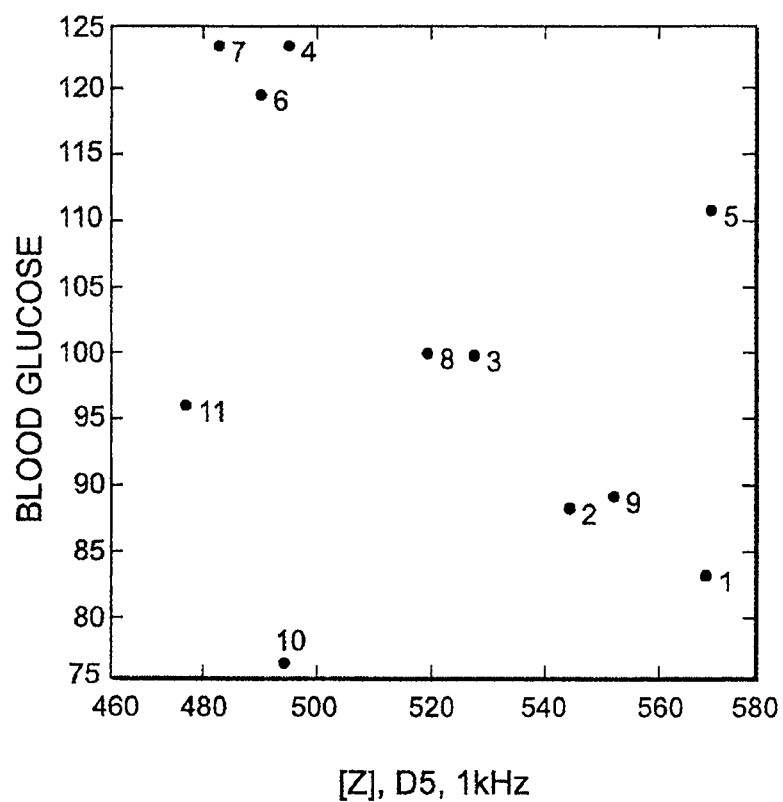
FIG. 7 shows a scatter plot of subject B's magnitude at 1 kHz and depth setting number 5 vs. blood glucose.
Figure 8A:
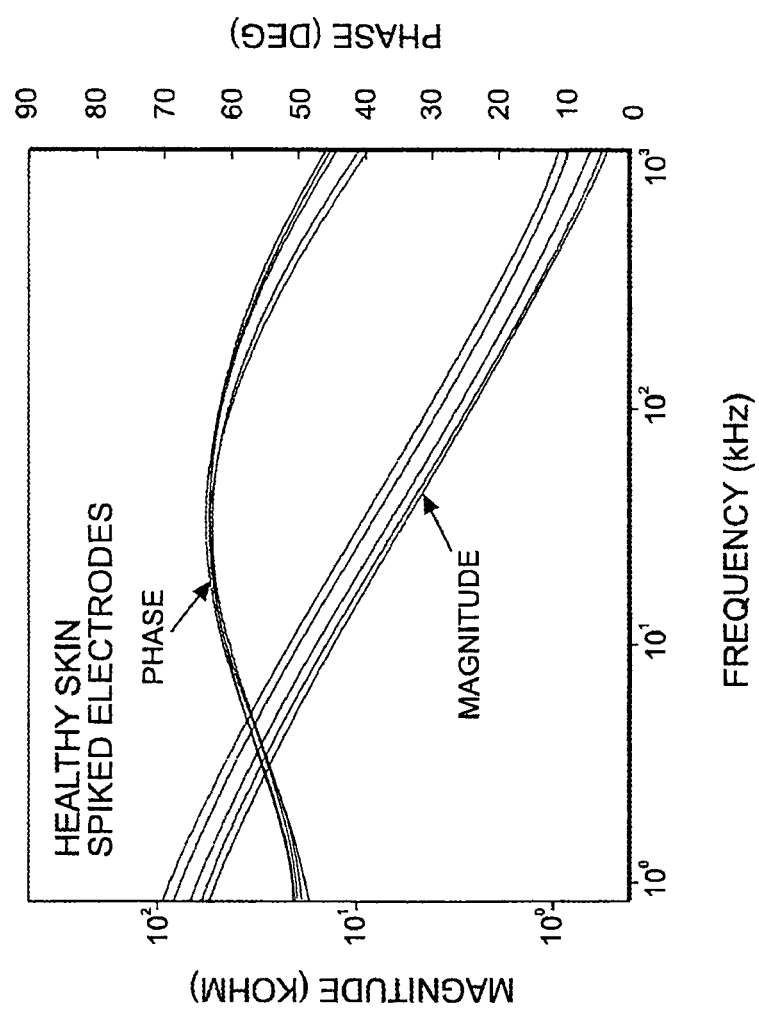
In FIG. 8(a), the results were obtained for a normal skin site of a subject.
Figure 8B:
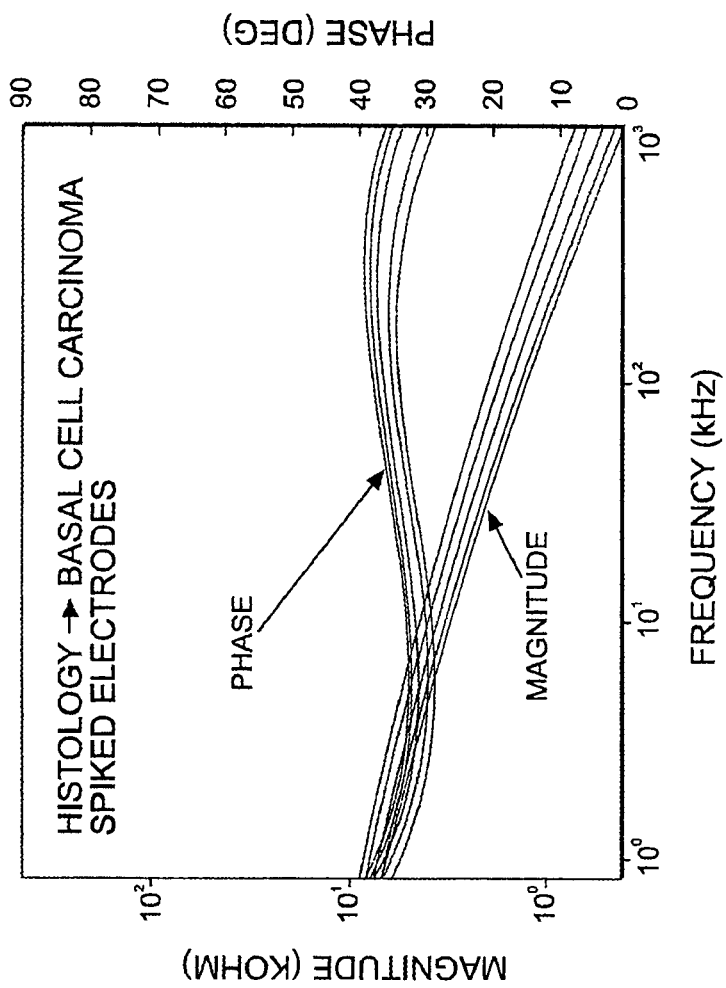
In FIG. 8(b), the results were obtained from the same subject but a basal cell carcinoma located near the normal site of FIG. 8(a).
Figure 8C:
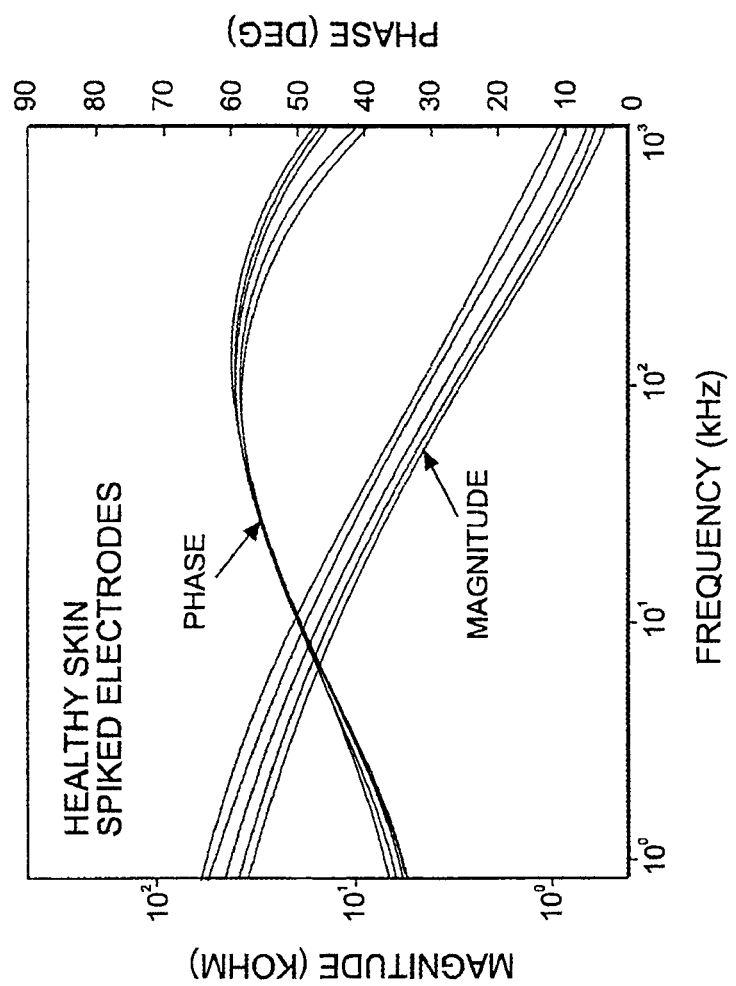
In FIG. 8(c), the results were obtained from a normal skin site of another subject.
Figure 8D:
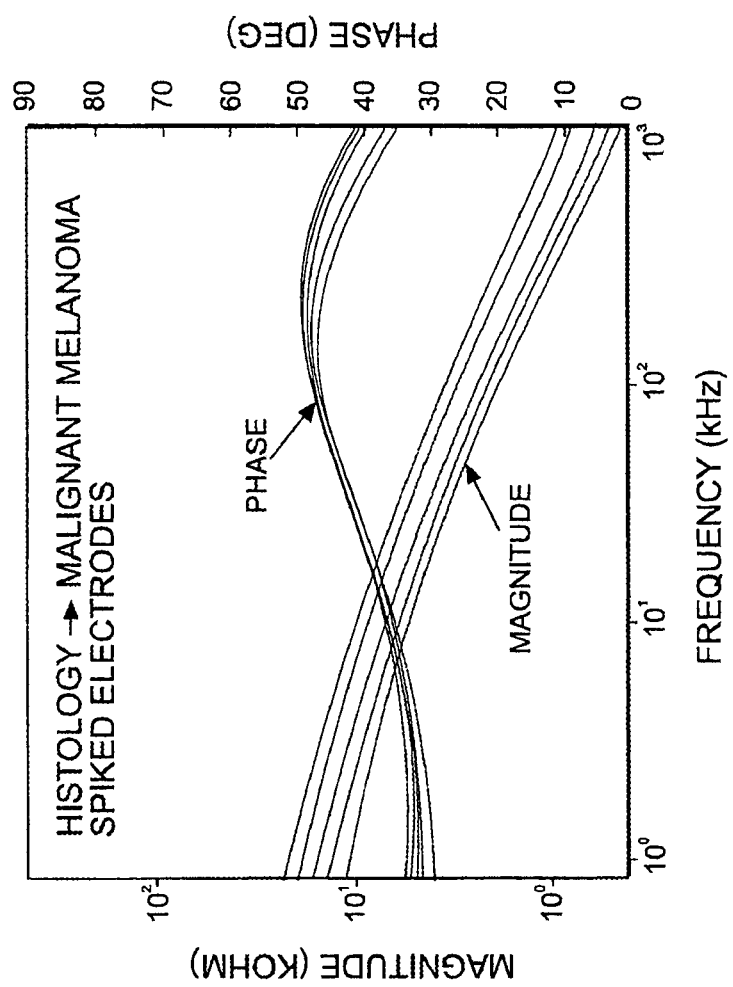
In FIG. 8(d), the results were obtained from this other subject but a malignant melanoma located near the normal site of FIG. 8(c). Each ensemble of curves represents five measured depths.

No significant impedance/glucose correlation was found using the conventional concentric probe if all the measurements were included. However, three readings, number 5, 10, and 11, do not show the same impedance/glucose pattern as the others (FIG. 7). If these 3 readings are excluded, the correlation coefficient becomes approximately 95%. If these excluded readings are not considered outliers (there is nothing abnormal about their impedance or glucose levels), the correlation between impedance measured with the regular probe and blood glucose would not be significant. However, suitable inundation and data exclusion criteria that might exclude these flawed measurements thus permitting accurate glucose predictions using the conventional probe at least under certain conditions.

The results described herein, summarized in Table 1, establish the improved correlation between measured skin impedance and blood glucose levels obtainable using the spiked electrode described above. It is the experience of the inventors, that a higher correlation can be achieved using the conventional probe with optimization of inundation time of the sample site.

TABLE 1

Summary of the correlation coefficient (R2) between blood glucose and skin impedance measured with the regular probe and the spikes.

| Subject | Conventional Probe | Spiked Electrode |
|---------|-------------------|------------------|
| A       | Not significant   | ~70%             |
| B       | Not significant   | ~80%             |

It is evident that there was a strong correlation between skin impedance and blood glucose in this experiment. The correlation of the two subjects was found more reliable for the spiked electrodes than the conventional probe.

The spiked electrodes can improve the glucose correlation by mitigating factors interfering with the impedance tests and reducing the stringency of skin inundation in preparing the site for impedance measurement. Thus the spiked electrodes are likely to permit glucose determination more reliably in a wider variety of situations than such determination with a conventional probe.

The following inundation procedures can be used to improve results obtained with the conventional probe. Gauze inundation pads are kept in a closed beaker of 0.9% saline or packaged in a saturated state. The skin is inundated by holding the gauze pad in place at the test site for 40 seconds then wiping away any excess solution before the impedance test, with inundation again 10 additional seconds, wiping away any excess solution before the second impedance test and impedance test again. This procedure is repeated until a total of 70 seconds of inundation has been reached.

Figure 9:
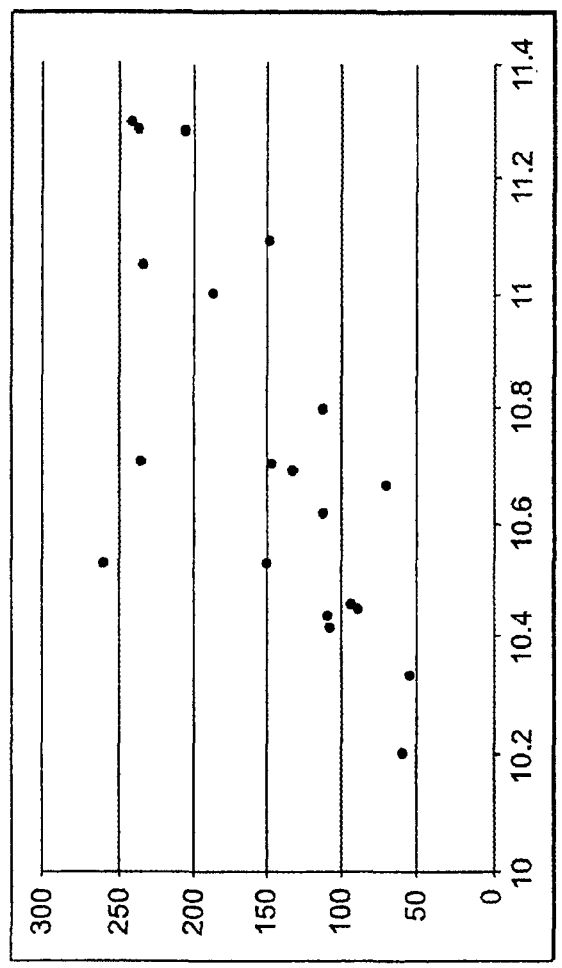
FIG. 9 shows a correlation between blood glucose and values obtained from impedance measurements taken using a multi-step inundation method and conventional electrode.

Data are included if at 1 Mhz at depth 1 the kOhms value is within the range 1.25 -1.45. Other frequencies can be used. If more than one impedance test was within this range, the kOhm value closest to 1.3 is selected. If the kOhm value is in range and IMIX at depth one value is between 10.2 and 11.5 then this IMIX value is accepted. Results obtained over several days are shown in FIG. 9.

The conditions under which reliable results are obtained using the probe having spiked electrodes are thus more relaxed than with the conventional probe. There is thus less likely to be a need for subjects to use a mild soap, for example, when using the spiked electrode. It may be possible to obtain reliable results with tanned or diseased skin (e.g., atopic dermatis) with the spiked probe where such was not possible with the conventional probe. It is also likely that use of the same site from measurement to measurement is less important when using the spiked probe than when using the conventional probe.

Cancer Diagnosis

Impedance measurements were similarly taken from subjects suffering from basal cell carcinoma or malignant melanoma: at a first site of normal (unaffected skin); and at a second site, of diseased skin. Results obtained are shown in FIG. 8. A further description of the approach, in which measurements were obtained using a conventional probe, is given in Emtestam I, Nicander I, Stenström M, Ollmar S. "Electrical impedance of nodular basal cell carcinoma: a pilot study", Dermatology 1998; 197: 313-316, and Kapoor S. "Bioelectric impedance techniques for clinical detection of skin cancer", (MSc-thesis) University of Missouri-Rolla 2001, and Åberg P, Nicander I, Holmgren U, Geladi P, Ollmar S. Assessment of skin lesions and skin cancer using simple electrical impedance indices. Skin Res Technol 2003; 9: 257-261, and Beetner D G, Kapoor S, Manjunath S, Zhou X, Stoecker W V. Differentiation among basal cell carcinoma, benign lesions, and normal skin using electric impedance. IEEE Trans Biomed Eng 2003; 50: 1020-1025.

It is desirable to detect and remove skin cancers as early as possible. As such, precursors of skin cancer, such as, for example, actinic keratose (a precursor of squamous cell carcinoma) and dysplastic nevi (a precursor of malignant melanoma), as well as other lesions that may be mixed up with various cancers unless surgery and histological evaluation of the catch is made, can be detected using impedance measurements of the present invention in the manner described herein.

The contents of all documents referred to herein are incorporated into this specification by reference as though such contents had been reproduced herein in their entirety.

The invention claimed is:

1. A method for diagnosing a diseased condition of the skin using an apparatus for the diagnosing of a diseased condition of the skin of a subject comprising an electrical probe for obtaining impedance data from a tissue region and an electronic control unit, the method comprising the steps of:
   (i) placing an electrical conducting probe against a skin surface of the subject, wherein the probe comprises at least three electrodes, each electrode furnished with a number of spikes, the spikes being laterally spaced apart from each other and being of sufficient length to penetrate the stratum corneum, wherein a first electrode and a second electrode of the at least three electrodes are spaced a first distance from each other and wherein the first electrode and a third electrode of said at least three electrodes are spaced a second distance from each other;
   (ii) using an electronic control unit connected to the probe to
      pass an electrical current through the electrodes, wherein said electrical current is separately passed between the first and the second electrode and between the first and the third electrode, measure a resulting voltage between the first and the second electrode and between the first and the third electrode, and determine a first value of impedance based on the electrical current between the first and second electrode and the resulting voltage between the first and second electrode and a second value of impedance based on the electrical current between the first and third electrode and the resulting voltage between the first and third electrode; and (iii) using reference data to determine whether the first and second impedance values indicate the diseased condition by comparing the first and second impedance values with the reference data.

2. The method of claim 1, wherein the diseased condition is cancer.

3. The method of claim 2, wherein said cancer is a skin cancer selected from the group consisting of basal cell sarcoma, malignant melanoma, squamous cell carcinoma, or precursors of such lesions.

4. A method according to claim 1, wherein each spike is at least 10 pm in length.

5. The method of claimer 1, wherein the first and second distances are different from each other.

6. The method of claim 1, wherein the first distance is between about 0.1 mm and about 40 mm; or between about 0.1 mm and 30 mm; or between about 0.1 mm and 25 mm; or between about 0.1 mm and 20 mm; or between about 0 1 mm and 15 mm; or between about 0.2 mm and 10 mm; or between about 0.2 mm and 8 mm; or between about 0.2 mm and 5 mm; or between about 0.2 mm and 3 mm; or between about 0.2 mm and 2 mm; or between about 0.2 mm and 1.5 mm; or between about 0.2 mm and 1 mm; or between about 0.2 mm and 0.5 mm.

7. The method of claim 6, wherein the second distance is between about 1 mm and about 50 mm; or between about 1 mm and 40 mm; or between about 1 mm and 30 mm; or between about 1 mm and 25 mm; or between about 1 mm and 20 mm; or between about 1 mm and 15 mm; or between about 1 mm and 10 mm; or between about 1 mm and 9 mm; or between about 1 mm and 8 mm; or between about 1 mm and 7 mm; or between about 2 mm and 8 mm; or between about 3 mm and 7 mm; or between about 4 mm and 7 mm; or between about 4 mm and 6 mm; or about 5 mm.

8. The method of claim 1, wherein for each electrode, there are at least two said spikes, or at least three said spikes, or at least four said spikes, or at least five said spikes, or at least six said spikes, or at least seven said spikes, or at least eight said spikes, or at least nine said spikes, or at least ten said spikes, or at least twelve said spikes, or at least fifteen said spikes, or at eighteen said spikes, or at least twenty said spikes, or at least twenty-five said spikes, or at least thirty said spikes, or at least thirty-five said spikes, or at least fifty said spikes.

9. The method of claim 1, wherein each said spike is up to 250, or up to 240, or up to 230, or up to 220, or up to 210, or up to 200, or up to 190 or up to 180 or up to 170 or up to 160 or up to 150 or up to 140 or up to 130 or up to 120 or up to 110 or up to 100 pm in length.

10. The method of claim 1, wherein each said spike is at least 20, or at least 30 or at least 40 or at least 50, or at least 60 or is at least 70 or is at least 80 or is at least 90 pm in length.

11. The method of claim 1, wherein each said spike is of sufficient length to penetrate below the skin surface to the stratum germinativum or through the stratum corneum into the living epidermis but not into the dermis.

12. The method of claim 1, wherein the outer diameter of each spike is between about 20 pm and about 50 pm.

13. The method of claim 1, wherein said electrical current has a frequency of between about 10 Hz and about 10 MHz.

14. The method of claim 13, wherein step (ii) is conducted a first time at a first said frequency, and step ii is conducted a second time at a second said frequency.

15. The method of claim 1, wherein both non-invasive surface electrodes (conventional probes) are used in conjunction with said minimally invasive spiked electrodes to catch more aspects of skin properties in order to improve power of discrimination.

16. The method of claim 1, wherein said electrical current is passed between the first electrode and the second electrode and between the first electrode and the second electrode at different time.

17. An apparatus for the diagnosing of a diseased condition of the skin of a subject, said apparatus comprising:

an electrically conducting probe including at least three electrodes for obtaining impedance data from a tissue region, each electrode comprising at least one spike, which spikes are laterally spaced apart from each other and having a length being sufficient to penetrate the stratum corneum, wherein a first electrode and a second electrode of the at least three electrodes are spaced a first distance from each other and wherein the first electrode and a third electrode of said at least three electrodes are spaced a second distance from each other, and an electronic control unit connected to the probe and configured to, when the probe is placed against a skin surface of the subject such that said spikes penetrate the stratum corneum, pass an electrical current through the electrodes, wherein said electrical current is separately passed between the first and the second electrode and between the first and the third electrode, measure a resulting voltage between the first and the second electrode and between the first and the third electrode, determine a first value of impedance based on the electrical current between the first and second electrode and the resulting voltage between the first and second electrode and a second value of impedance based on the electrical current between the first and third electrode and the resulting voltage between the first and third electrode, and use reference data to determine whether the impedance values indicate the diseased condition by comparing the first and second impedance values with the reference data.

18. The apparatus according to claim 17, wherein the diseased condition is cancer.

19. The apparatus according to claim 18, wherein said cancer is skin cancer selected from the group consisting of basal cell sarcoma, malignant melanoma, squamous cell carcinoma, or precursors of such lesions.

20. The apparatus according to claim 17, wherein each spike has a length of at least about 10 pm.

21. The apparatus according to claim 17, wherein said first distance and said second distance are different from each other.

22. The apparatus according to claim 17, wherein said first distance is between about 0.1 mm and about 40 mm; or between about 0.1 mm and 30 mm; or between 0.1 mm and 25 mm; or between about 0.1 mm and 20 mm; or between 0.1 mm and 15 mm, or between about 0.2 mm and 10 mm; or between about 0.2 mm and 8 mm; or between about 0.2 and 5 mm; or between about 0.2 mm and 3 mm; or between about 0.2 mm and 2 mm; or between 0.2 mm and 1.5 mm; or between about 0 2 mm and 1 mm; or between about 0.2 mm and 0.5 mm.

23. The apparatus according to claim 17, wherein said second distance is between about 1 mm and about 50 mm; or between about 1 mm and 40 mm; or between about 1 mm and 30 mm; or between about 1 mm and 25 mm; or between about 1 mm and 20 mm; or between about 1 mm and 15 mm; or between about 1 mm and 10 mm; or between about 1 mm and 9 mm; or between about 1 mm and 8 mm; or between about 1 mm and 7 mm; or between about 2 mm and 8 mm; or between about 3 mm and 7 mm; or between about 4 mm and 7 mm; or between 4 mm and 6 mm; or about 5 mm.

24. The apparatus according to claim 17, wherein each electrode comprises at least two said spikes; or at least three said spikes; or at least four said spikes; or at least five said spikes; or at least six said spikes; or at least seven said spikes; or at least eight said spikes; or at least nine said spikes; or at least ten said spikes; or at least twelve said spikes; or at least fifteen said spikes; or at least eighteen said spikes; or at least twenty said spikes; or at least twenty-five said spikes; or at least thirty said spikes; or at least thirty-five said spikes; or at least fifty said spikes.

25. The apparatus according to claim 17, wherein each of said spikes has a length up to about 250 pm, or up to 240 pm, or up to 230 pm, or up to 220 pm, or up to 210 pm, or up to 200 pm, or up to 190 pm, or up to 180 pm, or up to 170 pm, or up to 160 pm, or up to 150 pm, or up to 140 pm, or up to 130 pm, or up to 120 pm, or up to 110 pm, or up to 100 pm.

26. The apparatus according to claim 17, wherein each spike is at least 20; or at least 30; or at least 40; or at least 50; or at least 60; or at least 70; or at least 80, or at least 90 pm in length.

27. The apparatus according to claim 17, wherein each of said spikes has a length being sufficient to penetrate below the skin surface to the stratum germinativum or through the stratum corneum into the living epidermis but not into the dermis.

28. The apparatus according to claim 17, wherein an outer diameter of each of said spikes is between about 20 pm and about 50 pm.

29. The apparatus according to claim 17, wherein said electrical current has a frequency between about 10 Hz and about 10 MHz.

30. The apparatus according to claim 17, wherein said apparatus is adapted to use both non-invasive surface electrodes in conjunction with said spiked electrodes to obtain more aspects of skin properties in order to improve power of discrimination.

* * * * *